(12) United States Patent
Lienard et al.

(10) Patent No.: US 7,065,395 B2
(45) Date of Patent: Jun. 20, 2006

(54) METHOD AND APPARATUS FOR CARDIAC RADIOLOGICAL EXAMINATION IN CORONARY ANGIOGRAPHY

(75) Inventors: Jean Lienard, Igny (FR); Regis Vaillant, Villebon sur Yvette (FR); Francisco Sureda, Chatenay Malabry (FR); Laurent Launay, Saint Remy les Chevreuse (FR)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 225 days.

(21) Appl. No.: 10/295,055

(22) Filed: Nov. 4, 2002

(65) Prior Publication Data

US 2003/0069499 A1    Apr. 10, 2003

Related U.S. Application Data

(63) Continuation of application No. PCT/US02/08104, filed on Mar. 15, 2002.

(30) Foreign Application Priority Data

Mar. 19, 2001  (FR) .................................. 01 03699

(51) Int. Cl.
*A61B 6/00* (2006.01)
(52) U.S. Cl. .................. 600/431; 600/428; 600/433; 600/435; 600/509; 378/23
(58) Field of Classification Search ............... 600/407, 600/420, 431–435, 413, 428; 128/920; 378/4, 378/8, 23, 27
See application file for complete search history.

(56) References Cited

U.S. PATENT DOCUMENTS

| | | | | |
|---|---|---|---|---|
| 4,006,736 A | | 2/1977 | Kranys et al. | 128/2 A |
| 4,611,340 A | | 9/1986 | Okazaki | 378/95 |
| 4,777,951 A | * | 10/1988 | Cribier et al. | 606/194 |
| 5,476,453 A | | 12/1995 | Mehta | 604/281 |
| 6,269,140 B1 | | 7/2001 | Takagi et al. | 378/8 |
| 6,337,992 B1 | | 1/2002 | Gelman | 600/425 |
| 6,442,415 B1 | * | 8/2002 | Bis et al. | 600/420 |
| 2001/0054695 A1 | * | 12/2001 | Lienard et al. | 250/368 |

FOREIGN PATENT DOCUMENTS

| | | |
|---|---|---|
| DE | 2500851 | 6/1976 |
| WO | 9315658 | 8/1993 |

* cited by examiner

*Primary Examiner*—Ruth S. Smith
(74) *Attorney, Agent, or Firm*—Cantor Colburn LLP

(57) ABSTRACT

A method of cardiac radiological examination for coronarography comprises the steps of:
 a) introducing contrast medium simultaneously in the left coronary artery and in the right coronary artery from the aortic root and, in parallel,
 b) acquiring a sequence of dynamic images of the propagation of the contrast medium in the left and right coronary arteries with a displacement of the image plane, during the acquisition of said images, along a determined trajectory (E28). The contrast medium can be introduced in a cyclic manner during the acquisition of dynamic images, each cycle of introduction corresponding to a phase of closure of the aortic valve in the cardiac rhythm. 3D and 4D images with optimal efficiency can be obtained in the use of contrast medium. An injection device for producing the above cycles is synchronized with the introduction of the contrast medium.

45 Claims, 9 Drawing Sheets

US 7,065,395 B2

METHOD AND APPARATUS FOR CARDIAC RADIOLOGICAL EXAMINATION IN CORONARY ANGIOGRAPHY

CROSS REFERENCE TO RELATED APPLICATIONS

This application is a continuation of international application number PCT/US02/08104, filed Mar. 15, 2002, which claims the benefit of a priority under 35 USC 119 to French Patent Application No. 0103699 filed Mar. 19, 2001, the entire contents of which are hereby incorporated by references.

BACKGROUND OF THE INVENTION

The invention concerns medical imaging in cardiology and, in particular, coronary angiography and, as the case may be, in ventriculography.

Radiological examinations in coronary angiography and ventriculography are usually carried out by dynamic filming from different fixed image planes around the heart, which constitute reference angulations. Several sequences of images are then obtained, typically for a few seconds each, making it possible to visualize as a whole, through those different planes, the structure of the coronary arterial tree, of the aorta and of the left ventricle, each plane offering a two-dimensional point of view.

The parts of interest are revealed by opacification by means of a contrast medium in liquid form introduced in well controlled areas. In order to perform those injections on a coronary angiography and venticulography examination, three different catheters are ordinarily used. A protocol according to which dynamic image sequences are obtained, each sequence being taken form a respective fixed plane.

The protocol as a whole is lengthy and labored owing to the fact that it requires successively introducing and withdrawing three different catheters, with an injection each time of contrast medium for each image plane. Furthermore, the total quantity of contrast fluid injected has to be limited because of its toxicity. The time allotted to the injections in the coronary arteries is therefore very short and may be insufficient to follow the progress of the product well. The protocol also has the disadvantage of requiring many repeated positionings of the source-detector tandem in order to make the different acquisitions, which also shortens the examination time. especially in the case of a cradle with manual displacement. As for costs, it is necessary to arrange, among other things, to make three different catheters available for a complete examination.

BRIEF DESCRIPTION OF THE INVENTION

The invention is directed to a protocol, i.e., method, of coronary angiographic imaging, possibly accompanied by ventriculographic imaging, which makes better use of the contrast medium possible and which is well suited to three-dimensional dynamic imaging.

In particular, the invention concerns a method of cardiac radiological examination in coronary angiography, comprising:

a) introducing a contrast medium simultaneously in the left coronary artery and in the right coronary artery from the root of the aorta and, in parallel, b) acquiring a sequence of dynamic images of propagation of the contrast medium in the loft and right coronary arteries with procession of the image plane, upon acquisition of images, on a given path.

The invention also concerns a device for injection of contrast medium in a catheter intended for cardiac radiology, which it is guided by a signal detecting cardiac rhythms, so as to inject-the contrast medium during cycles synchronized with given phases of the cardiac rhythm.

BRIEF DESCRIPTION OF THE DRAWINGS

The invention will be more clearly apparent, with reference to the attached drawings, in which.

DETAILED DESCRIPTION OF THE INVENTION

Figure 1:
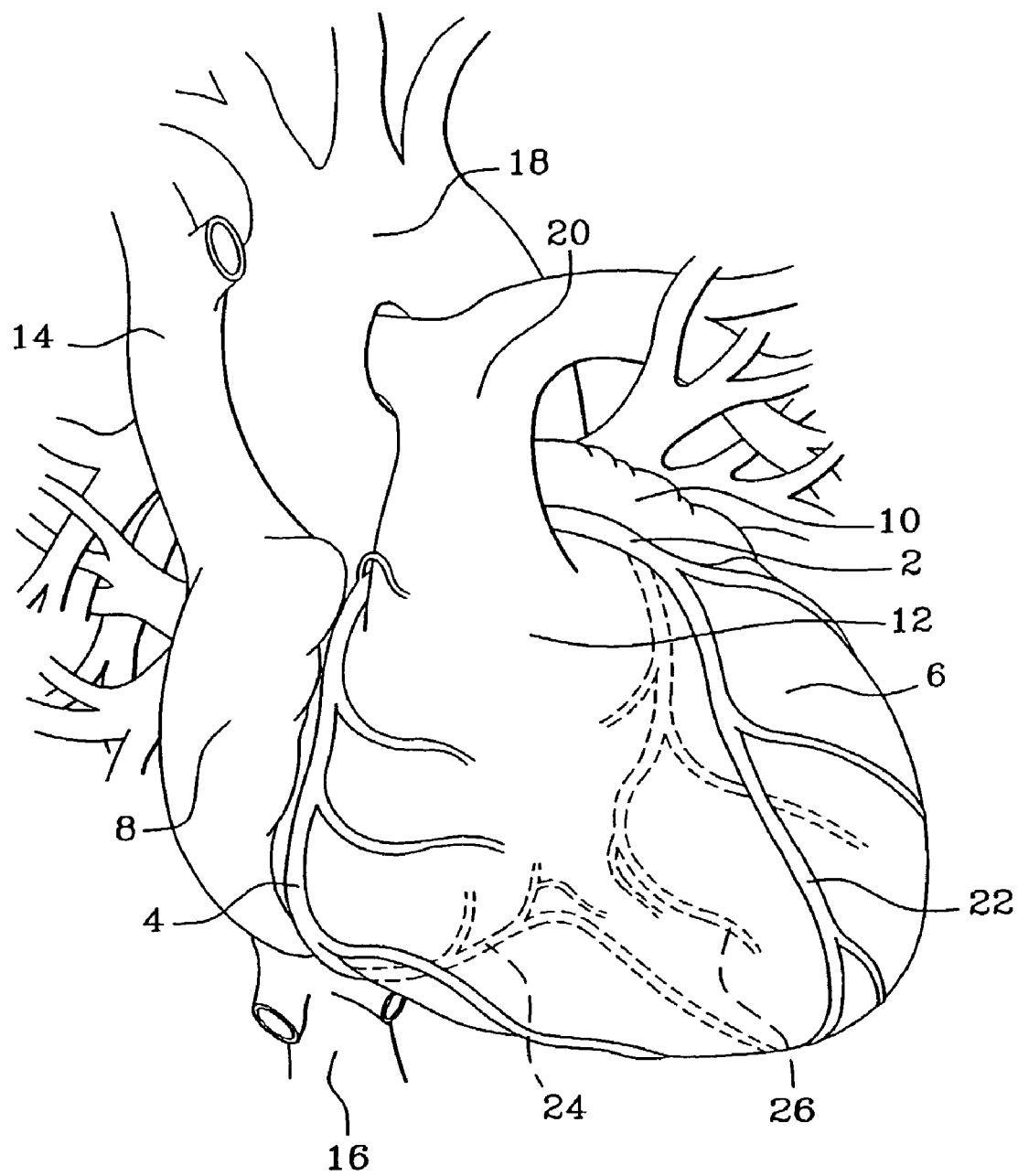
FIG. 1 is a general view of the heart.

The three different catheters are positioned respectively as shown in FIG. 1: the aperture of the left coronary artery 2, the aperture of the right coronary artery 4 and the interior of the left ventricle 6.

FIG. 1 further identifies in the heart: the right auricle 8, the left auricle 10, the right ventricle 12, the superior caval vein 14, the inferior caval vein 16, the aorta 18, the pulmonary artery 20, the anterior interventricular artery 22, the posterior interventricular artery 24 and the circumflex left artery 26.

Figure 2:
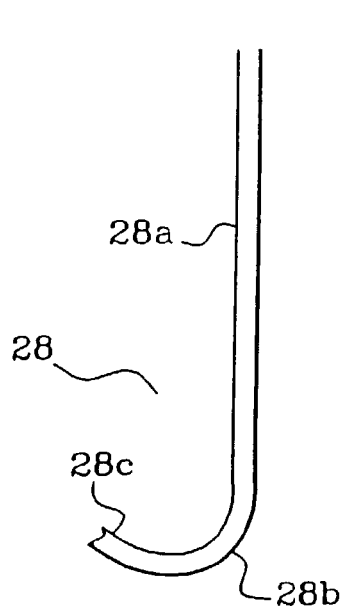
FIG. 2 is a view of the injection end of a catheter intended for the introduction of contrast fluid in the right coronary artery, used in the prior art.
Figure 3:
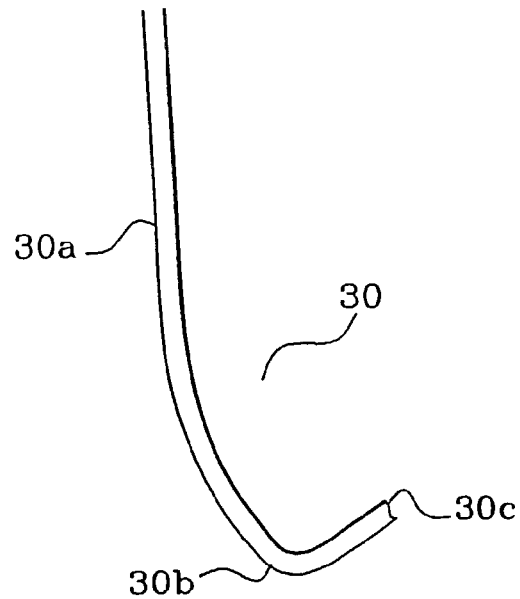
FIG. 3 is a view of the injection end of a catheter intended for the introduction of contrast fluid in the left coronary artery, used in the prior art.
Figure 4:
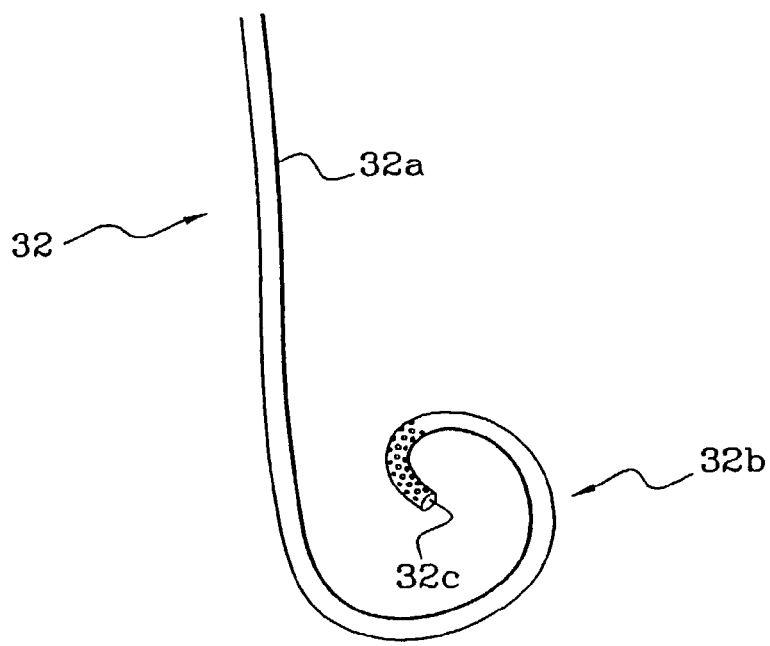
FIG. 4 is a view of the injection end of a "pigtail" catheter commonly used to introduce contrast fluid in the left ventricle.

FIGS. 2, 3 and 4 respectively show the shapes that the injection ends of the three aforementioned catheters take when deployed. The catheter 28 intended for the right coronary artery as shown in FIG. 2, presents an appreciably straight section 28a which ends in an elbowed portion 28b in order to guide the tip 28c to approximately 90° from the straight part 28a, so that it can partially enter the coronary artery. The tip 28c affords a single outlet for the contrast fluid, situated at its end point. The catheter 30 intended for the left coronary artery, as shown in FIG. 3. takes appreciably the same shape, but of opposite geometry, so that tip 30c can partially enter that coronary artery. The catheter 32 intended for the left ventricle, as shown in FIG. 4, presents, in the extension of an appreciably straight part 32a, a spiraled end 32b. By reason of that particular shape, this type of catheter is generally known as a "pigtail". The spiral shape ensures that tip 32c of the catheter does not come too close to or in contact with the walls of the left ventricle. In fact, catheter 32 is generally inserted "blind" and the contrast fluid is ejected there from tip 30c at a very high pressure, necessary to overcome the pressure prevailing in the ventricular cavity. The spurt of fluid could damage the wall if it were too close to the walls.

In contrast to catheters 28, 30 intended for the coronary arteries, the 32c of the pigtail catheter contains several outlets for the contrast fluid, uniformly distributed on the periphery of its wall just before its termination point. Hence, the contrast fluid is appreciably dispersed uniformly around the end portion and rapidly fills the cavity of the left ventricle.

Catheters 28, 30, 32 are introduced in the body from a part distant from the heart, generally from a peripheral artery or vein. The catheters are guided along the arteries by a wire contained inside and which keeps the injection ends appreciably straight until approaching the point of arrival. The wire is then withdrawn from the end to enable the latter to recover its adapted shape. The opposite end of the catheter is connected either to a manually operated syringe, in the case of catheters intended for the coronary arteries, or to an electrically controlled automatic injector, in the case of a pigtail catheter intended for the ventricle.

Figure 5:
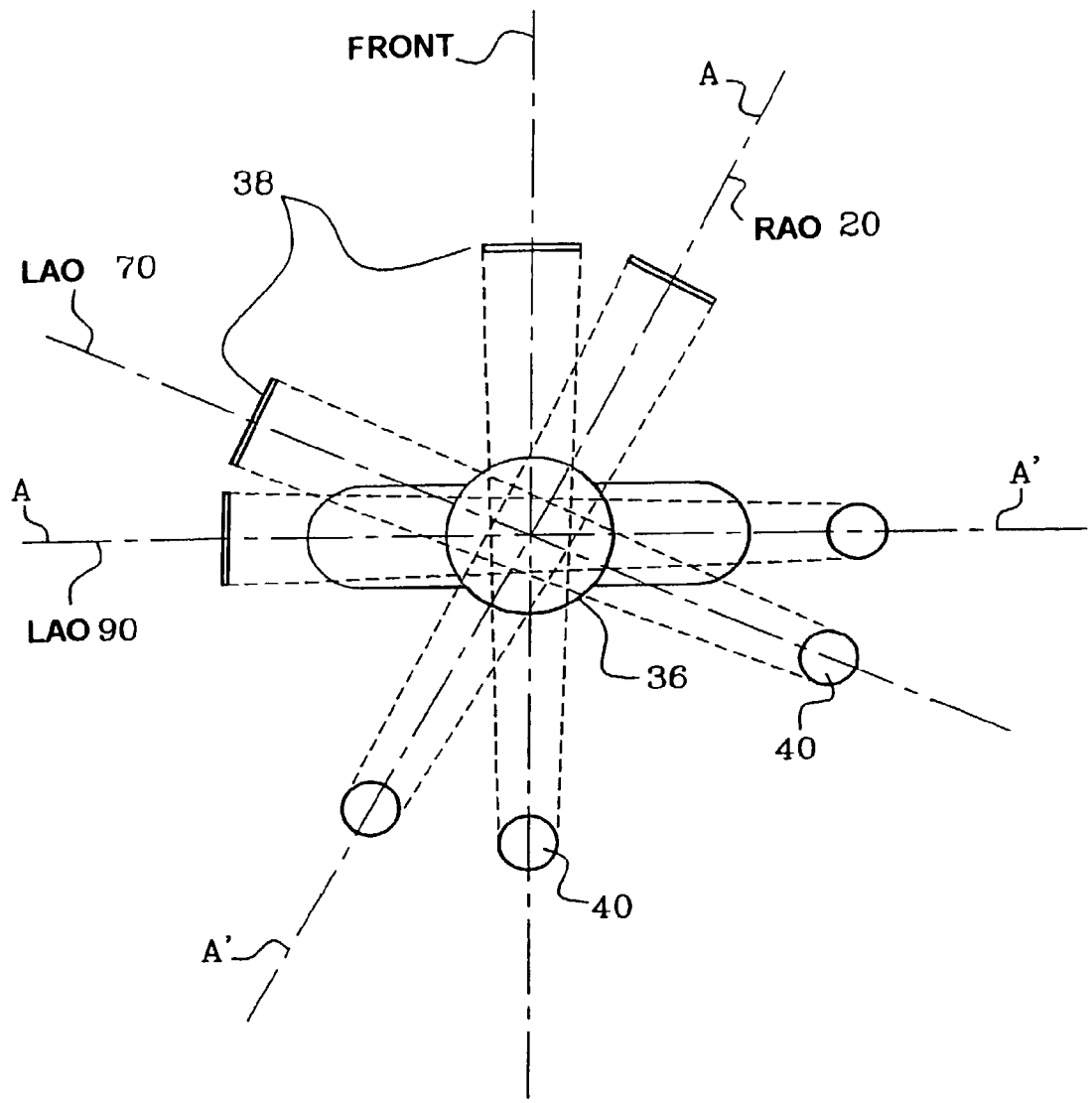
FIG. 5 is a diagram showing different angulations for radiological image acquisitions.
Figure 6:
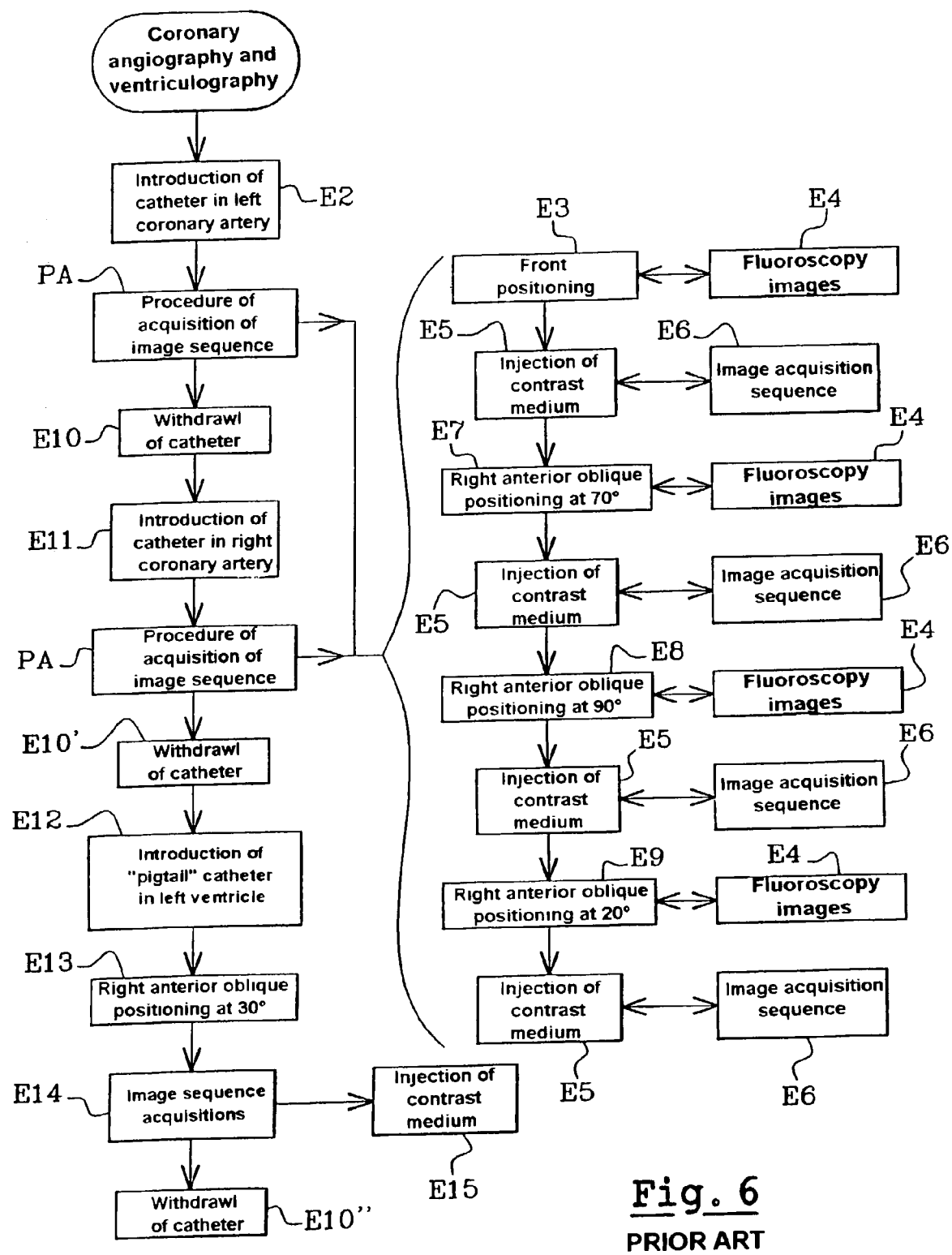
FIG. 6 is a flow chart showing the principal stages of a standard protocol of coronary angiography and ventriculography.

Referring to FIGS. 5 and 6, the standard protocol of image acquisition in coronary angiographic and ventriculographic radiography will now be described with use of catheters 28, 30 and 32.

As FIG. 5 shows schematically, the patient 36 (head and shoulders represented) is positioned stretched out in a radiology apparatus having a radiological image sensor 38 (film or electronic) and an X-radiation source 40. The tandem formed by the sensor 38 and the source 40 is aligned on an axis A–A' perpendicular to the head-to-toe axis (longitudinal) of the patient at chest level. The tandem is rotatable around the head-to-toe axis of the patient, the sensor 38 and the source 40 being normally mounted at the respective ends of a semicircular cradle in which the patient is centered. It is thus possible to take image acquisition sequences at different angles in the plane of rotation of the source-detector tandem.

FIG. 6 is a flow chart of the principal stages of the standard coronary angiography and ventriculography protocol, according to which dynamic image sequences are obtained, each sequence being taken from a respective fixed plane. The catheter 28 in the aperture of the left coronary artery (stage E2). Its positioning is generally made by touch on manipulation of the catheter. If necessary, a little contrast medium can be sent in during that stage to visualize the environment of the end of the catheter in fluoroscopy (real-time imaging under low dose without recording). Once the catheter 28 is positioned, a procedure of acquisitions (PA) of dynamic image sequences is undertaken, the principal stages of which are represented in the right part of FIG. 6. This PA procedure obtains and records several dynamic image sequences showing the progress of the contrast medium in the coronary artery, each taken on a different plane constituting a reference position (or angulation). Typically, the reference positions are as follows (cf. FIG. 5): (1) front, with the detector 38 directly facing the patient; (2) OAG 70[LAO 70], i.e., left anterior oblique projection at 70° (the direction is always referenced in relation to the patient); (3) OAG 90 [LAO 90], i.e., left anterior oblique projection at 90°, or strict profile, and (4) OAD 20 [RAO 20], i.e., right anterior profile at 20°.

For each sequence, a dosed quantity of contrast medium, normally about five cubic centimeters, is manually injected throughout the filming sequence. that is, over a period of five to six seconds. The rate of acquisition is 25 or 30 images per second (according to European or United States standards), giving a total in the order of 150 to 200 acquired images per plane.

The method begins by placing the source-sensor tandem 38, 40 for acquisition of the front sequence (stage E3). During the positioning, it is verified by fluoroscopy that the image plane is correctly framed and that the catheter is always well positioned (stage E4), making adjustments when necessary. Acquisition of the dynamic sequence is then controlled (stage E5) under X-rays and the contrast medium is simultaneously injected under the aforesaid conditions (stage E6). When acquisition is completed, the same procedure is undertaken for each of the following planes (OAG 70, OAG 90 and OAD 20), with the respective positioning stages (E7, E8, E9). Altogether, approximately 20 seconds of dynamic sequences of the left coronary artery are thus acquired, with a total dose in the order of 20 cubic centimeters.

The catheter 28 is then withdrawn (stage E10) and, in its place, the catheter 30 intended for the right coronary artery is introduced in the aperture of the latter (stage E11). The PA procedure of acquisitions of dynamic sequences described above is then restarted. That PA procedure can possibly be modified at the reference positions in order to better suit the configuration of the structure of the right coronary artery. After the sequence acquisitions for the right coronary artery, the catheter is withdrawn (stage E10').

The method continues with ventriculography by introduction of the pigtail catheter 32 in the cavity of the left ventricle (stage E12), with a right anterior oblique positioning of the image plane at 30° (OAD 30) (stage E13). The acquisition of a dynamic image sequence is then begun over a period in the order of three or four seconds (stage E14). During that acquisition approximately 40 cubic centimeters of contrast medium is injected by means of an electromechanical injector (stage E15). Exploration of the ventricle makes it possible to visualize its general shape and to observe the manner in which it is contracted. In some cases, views are also acquired in the OAG 60 axis, when it is a question of detecting anomalies of movement of the wall of the septum. Finally, the catheter 32 is withdrawn on completion of the examination protocol (stage E10").

Embodiments of the invention are presented within the context of a radiology apparatus which enables displacements of the source-detector tandem to be made along a so-called "left" curve (i.e., not situated on a single plane), as described in FR00 07155. However, the invention can also be used with a standard radiological imaging apparatus.

Figure 7:
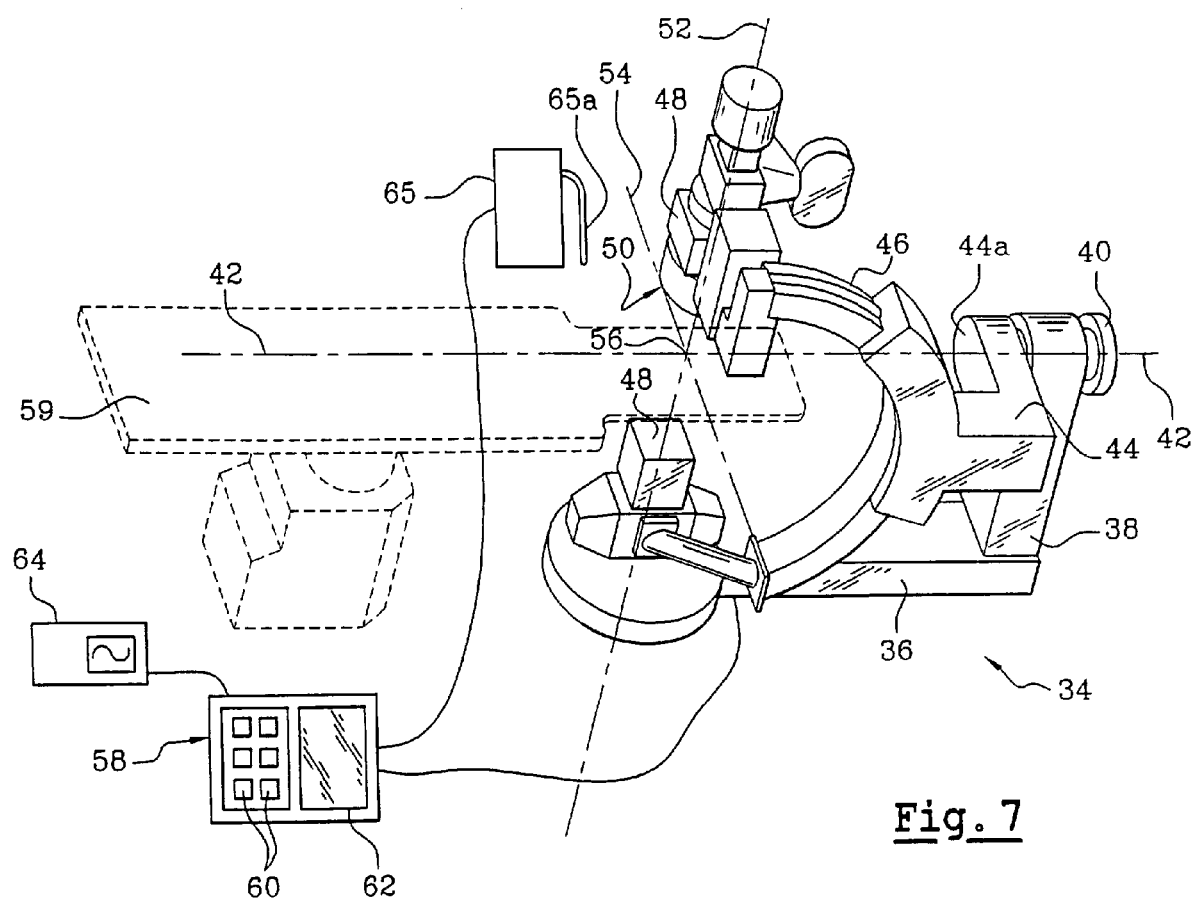
FIG. 7 is a general view of a radiography apparatus, with schematic representation of accessories, according to an embodiment of the invention.

As FIG. 7 shows, the apparatus 34 comprises a bearing structure comprising a flat base 36 standing on the floor, with a support wall 38 at right angles to that base. The support wall maintains at a raised level a rotary shaft 40 aligned on a horizontal axis 42. Shaft 40 fits laterally into the end 44a of a rotary support arm 44 of a semicircular cradle 46, to the free ends of which an X-ray source 48 and a detector 50 are respectively attached. The support arm 44 is L-shaped, so that the axial displacement of the cradle 46 produced by the branch of the L perpendicular to the horizontal axis 42 compensates for the laterally offset mounting of the source 48 and detector 50 on the cradle 46. Hence, the axis 52 connecting the source 48 to the detector 50 crosses the axis of rotation 42. The cradle 46 is in turn mounted sliding on the support arm 44 to afford a circumferential rotation. The sliding thus makes it possible to displace the position in space of the source-detector axis 52 around a sliding axis 54 centered on the cradle 46. The respective axes 42, 52 and 54 of rotation of the support arm 44, of source-detector alignment 48, 50 and of sliding are secant at a point 56 called isocenter and are mutually perpendicular (orthogonal). The patient is maintained in a horizontal plane on a table 59 aligned with the horizontal axis 42.

The arrangement of axes 42, 52 and 54 permits a three-dimensional displacement in space of the source-detector tandem 48, 50 with degrees of freedom on two perpendicular planes, respectively aligned with the craniocaudal axis and with the right-left axis of the patient. The movements in each of these degrees of freedom are controlled independently by means of respective programmable actuators (not represented), although it is possible to form paths of the axis 52 of the source-detector tandem 48, 50 following left surfaces. The element of interest for that path being the sensitive surface of the detector 50, a path will be defined below in terms of displacement of the center of the image plane, comparable to the center of that sensitive surface 50. This central point therefore captures the radiation coming from the focal point of the source 48 after having crossed the patient at the isocenter 56.

It is also possible to have programming displacements of the image plane on a path which turns around the craniocaudal axis and is displaced toward the patient's head or feet on approaching its front view.

The entire operation of the apparatus 34 is managed by a microprocessor-based control unit 58 with an access console for the different functions 60 and a screen 62 for visualization of the different parameters and radiological images acquired. In the embodiment, the control unit is connected to an electrocardiograph machine 64 in order to synchronize certain actions with the movements of the heart and to an electromechanical injector 65 of contrast fluid having an injection tube 65a intended to fit into a catheter 32.

The functionalities managed by the control unit 58 are: (1) the respective actuators for the displacements of the source-detector tandem 48, 50 around axes 42, 54, with programming of: the path along a left (or flat) curve, the course of the rate of displacement (accelerations, decelerations) and stops on the path; (2) filming parameters: control of activation of the source and detector; and (3) operation of the injector 65, including control of an injection sequence divided into several injection cycles, with the following parameters: the start and interruption of an injection sequence synchronized with the start and stop of the image acquisition sequence, the beginning and end of each injection cycle as a function of the electrocardiogram (ECG) delivered by the electrocardiograph machine 64, the number of injection cycles and the injection delivery.

The control unit 58 also calculates a path and/or to memorize it. The path can be calculated from angulations, which can be indicated either by the user via the console 60 or by manually positioning the mobile unit of the apparatus 34 according to that angulation and memorizing it. For example, by defining an angulation by three angles along the three three-dimensional marking axes 42, 52 and 54 linked to the apparatus 34, the user can, for instance, define a first angulation of coordinates (0, 0, 0), a second angulation of coordinates (0, 0, α) and a third angulation of coordinates (0, 0, β) with α and β not nil. The path can, of course, be programmed on a greater number of angulations. The control unit 58 then determines a path to be followed by the moving parts of the apparatus, by controlling the actuators in an appropriate manner, in order to make the image plane 50 pass through the angulations programmed, while taking into account the characteristics of the apparatus, such as: (1) possible angulations prohibited, because of the risk of causing collisions with the table 59, the patient, the source 48 or the detector 50, and (2) the mechanical or electromechanical stresses of the apparatus, such as maximum angular acceleration for each axis and the travel time, which should be as short as possible in order to minimize the total dose of contrast fluid to be injected.

In the disclosed embodiment, the path is programmed to describe a first passage around the patient in the left-right direction, followed by a second passage in the right-left direction, or vice versa, in order to define a loop. The loop can be open (end point not matching the starting point) or closed (end point matching the starting point). The rate of displacement of the image plane on the path is further programmed to be reduced on passages at angulations corresponding to chosen reference planes and increased between those points. Furthermore, the displacement of the image plane along the path is controlled with the electrocardiograph machine, so that the arrival at a reference plane systematically occurs at the time the heart is in a same given phase of its cycle, for example, the filling phase. That control is accomplished by an analysis of the electrocardiogram (ECG) produced by the electrocardiograph machine 64, the periodicity of which makes it possible to anticipate the different phases.

Figure 8:
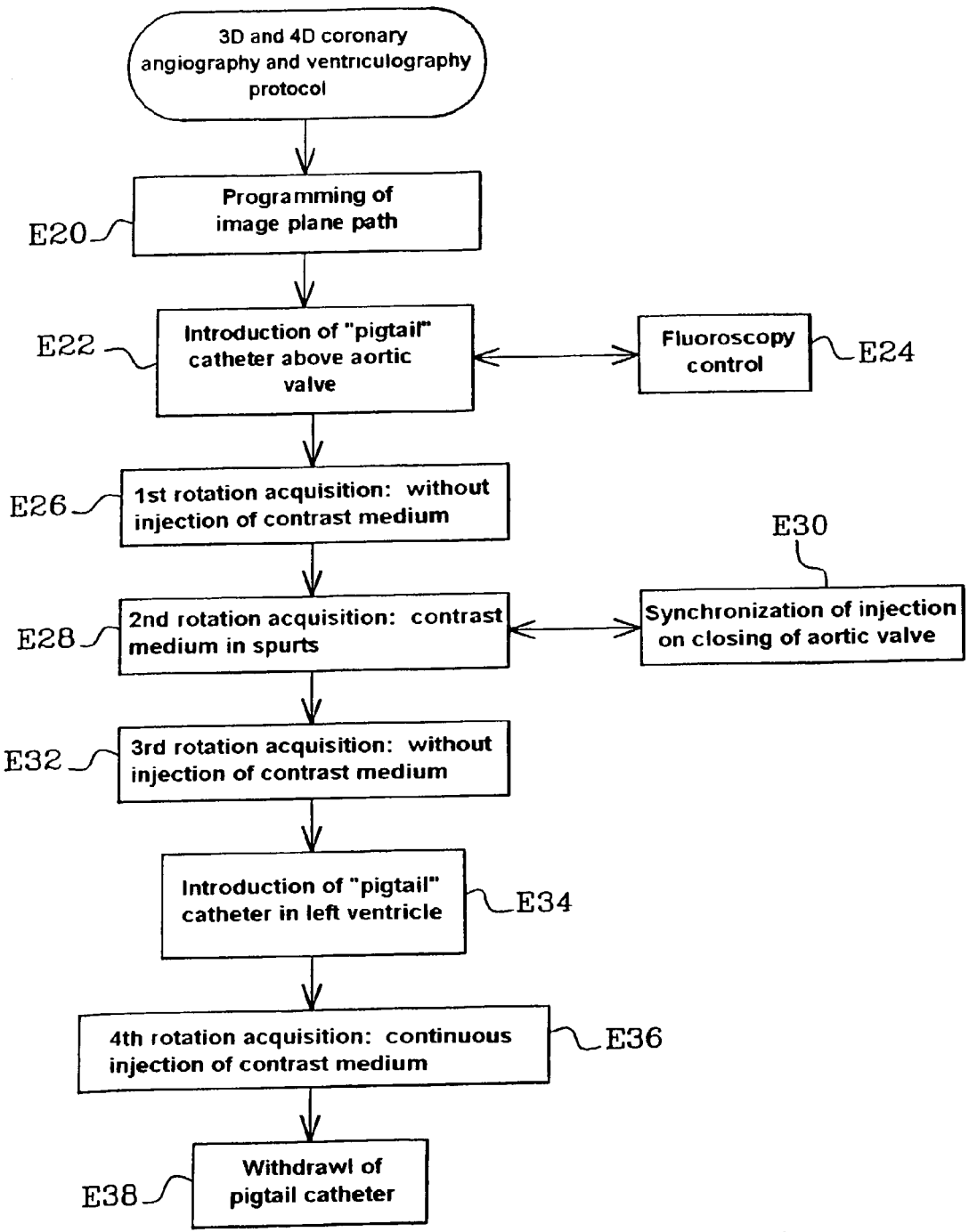
FIG. 8 is a flow chart showing the principal stages of a coronary angiography and ventriculography protocol according to an embodiment of the invention.

The protocol of coronary angiographic examination according to an embodiment of the invention, made with the apparatus of FIG. 7 so programmed, will be described by reference to the flow chart of FIG. 8 and to FIGS. 9 to 12. In the disclosed embodiment, the examination is followed by a ventriculographic examination. The sequences of acquired dynamic images make it possible to obtain by reconstruction three-dimensional (3D) images which evolve in time, giving rise to so-called four-dimensional (4D) images.

An initial phase of programming of the path of the image plane (stage E20) is provided. The programming starts with the location of positions of the image plane which are going to constitute reference angulations. These reference angulations are represented by large dots P1–P5 in FIG. 9, which is a spherical chart representing the different movements of the image plane. The center of the sphere is the isocenter 56 (FIG. 7) and its radius is equal to the distance between the isocenter and the focus of the X-ray source 48. The reference angulations include in part those commonly used in coronary arteriography (cf. FIG. 5), to which are added others chosen for an optimization of the points of view of the areas to be explored. For that purpose, it is taken into account that those angulations are used for imaging of both the left coronary artery and the right coronary artery. It is to be noted that the positions of reference angulations P1–P5 are freely chosen around the patient's craniocaudal axis 42 and right-left axis 54. In the disclosed embodiment, the angulations number five and include two "standard" angula-tions (on a same plane of rotation around the craniocaudal axis), namely: left anterior oblique at 60° (OAG 60) (point P1) and "frontal," where the axis of the X-ray beam is vertical, with the image plane positioned directly above the patient (point P2). A third angulation (point P3) corresponds to the OAG 30 image plane, but with a caudal deflection of 15°.

To those three angulations, two others are added, P4 and P5, chosen, for example, to better discern the structure of the right coronary artery.

In general, the following reference points can be considered. For a good visualization of the left coronary artery, a reference position in right anterior oblique view at 30° makes it possible to analyze the circumflex branch and a part of the left anterior descending artery. Another reference position on angulation of slightly caudal type, i.e., with the detector 50 close to the patient's feet, while maintaining the azimuth angle of 30°, can be used to visualize another part of the left anterior descending artery and to avoid having it covered on the image by the circumflex branch of the intermediate vessels. Conversely, a reference position in cranial-type angulation on right anterior oblique projection makes possible a good visualization of the diagonal arteries.

The reference position in left anterior oblique angulation at 60° can be used for study of the diagonal arteries and of a part of the anterior interventricular artery (IVA). With a cranial angulation at 20°, the left anterior oblique angulation at 60° can be applied to avoid shortening of a part of the IVA and provides good images of the left main trunk and diagonal branches. In side view, i.e., with the axis of the X-ray beam horizontal, particularly in left side view, another part of the IVA and the different parts of the first diagonal artery and of the marginal artery of the left edge can be optimally seen.

For the right anterior artery, a reference position in angulation of left anterior oblique type at 45° can be used associated with a caudal angle of 15°. The reference position in left anterior oblique angulation at 90° with caudal deflection of 15° can be used for analysis of the vertical part of the right coronary artery and collateral branches, right ventricular artery and right edge marginal artery. The reference position in right anterior oblique angulation at 45° with caudal deflection of 15° can be used for visualization of the posterior interventricular artery and collateral branches, right ventricular artery and right edge marginal artery.

Figure 9:
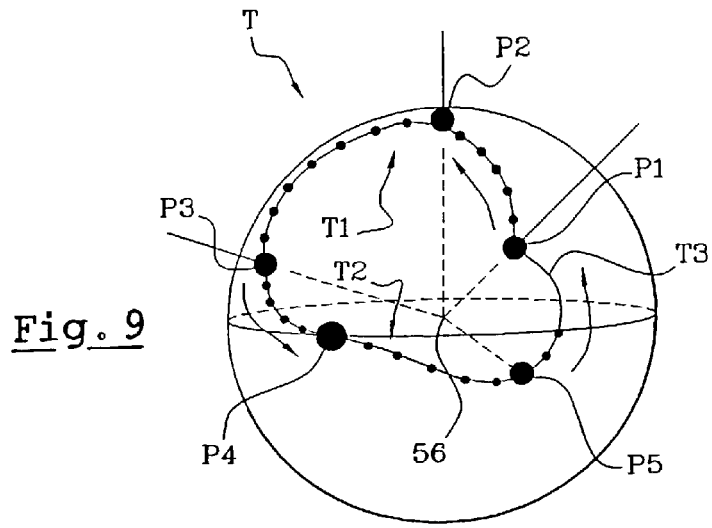
FIG. 9 is a schematic representation of the path and reference angulations for the rotation acquisitions that can be used in the protocol of FIG. 8.

When the reference angulations P1–P5 have been programmed, the control unit 58 calculates a path which passes over each of them. As shown in FIG. 9, that path, globally designated by T, consists of three parts which are linked together without interruption, namely: (1) a first part T1 corresponding to the left-right displacement of the image plane in a first direction (outward) and around the craniocaudal axis, beginning at angulation P1 and ending at angulation P3; (2) a second part T2 corresponding to the right-left displacement of the image plane in a second direction (inward) and around the craniocaudal axis, beginning at angulation P3 and ending at angulation P5; and (3) a third part T3 which joins angulations P5 to P1.

The displacement of the image plane on that whole path will be designated by the term "rotation," the filming and recording of images on a rotation being designated by the term "rotation acquisition."

The third part T3 of the path serves essentially to create a closed loop, i.e., to bring the image plane back to the starting point. In that way, it is possible to perform a succession of rotations without interruption.

The path T is calculated to produce a fluid movement of the image plane, with phases of acceleration at the start and deceleration at the approach of each reference angulation P1–P5. The movement is further subject to the ECG, so that the rapid displacements between two reference angulations occur during the diastole phase (when the heart is in quasi-stationary phase) and the slow passages at the reference angulations occur during the systole phase of the heart. Furthermore, synchronization on the ECG ensures that the heart will be in the same phase on passage at each of the reference angulations P1–P5.

By way of indication, the duration of the dynamic acquisition sequence on a rotation acquisition corresponds to four or five heart beats, that is, approximately five seconds. During the acquisition sequence, the source 48 and the detector 50 are activated with suitable adjustments of X-ray emission and filming.

The acquisition sequence covers the entire duration of the first and second parts T1, T2 of the path and possibly an initial portion of the third part T3. The acquisitions are made at a rate of 25 or 30 images per second. The portions of the path on which the images are acquired are symbolized by a series of small dots in FIG. 9.

In general, the programming stage E20 is executed only on initialization of the apparatus 34 for the protocol; that stage is therefore omitted for the examinations on the following patients, except in case of change of parameters.

Figure 10:
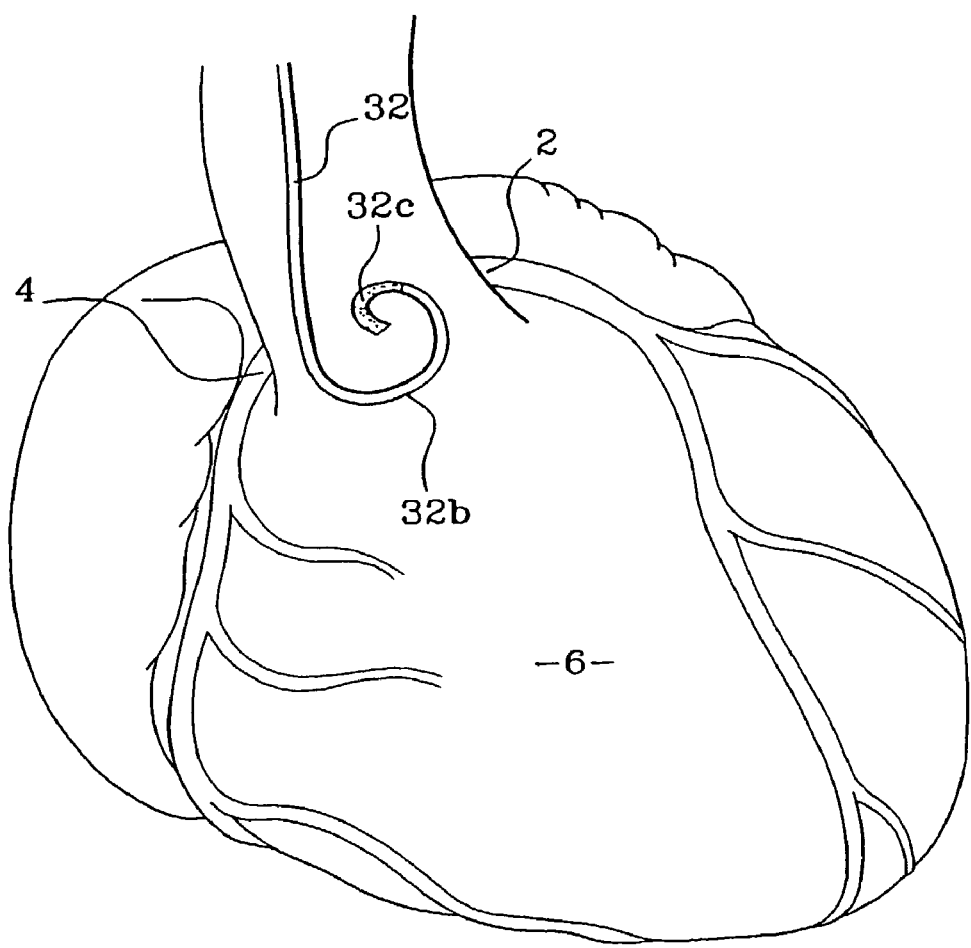
FIG. 10 is a view showing the positioning of the pigtail catheter in proximity to the left and right coronary arteries upon the introduction of contrast fluid for the second rotation acquisition of FIG. 8.

The examination proper then begins with the patient positioned on the table 59 and the introduction of a "pigtail" catheter 32, of gauge 6, for example, from the femoral artery to the aortic root, at the starting points of the left and right coronary arteries (stage E22). The positioning of the injection end of the catheter 32 is represented in FIG. 10. If necessary, the proper positioning of the catheter can be controlled on a fluoroscopy screen (stage E24).

Once the catheter 32 is positioned, a first rotation acquisition is executed on the path T with the characteristics of acceleration-deceleration and ECG synchronization, as described above, and without injection of contrast medium (stage E26). That sequence without opacification makes possible the acquisition of reference images for digital image subtraction. It also makes it possible to visualize the patient's anatomical structures, notably, the general positioning of the heart relative to the thorax and to the vertebral column. A representation of one of the images acquired during that first rotation acquisition is given in FIG. 11 (image I).

A second rotation acquisition identical to the first is then made, but with injection of contrast medium (stage E28). For that purpose, the catheter 32 is connected to the tube 65a of the injector 65, the latter being filled with contrast medium and capable of responding to the injection commands coming from the control unit 58. Thus, on injection of contrast medium, the latter is emitted with appreciably isotropic force and reaches the aperture of each of the left and right coronary arteries in order to be propagated along the coronary arterial tree. In the disclosed embodiment, the injection of contrast medium is not carried out continuously, but rather in spurts synchronized with the heart rate, so that the product is introduced on closing phases of the aortic valve (concomitant phase E30). The synchronization of the injection will be more specifically described by reference to FIG. 12. The peaks 66 of the ECG wave 68 indicative of diastole (dilation) are identified in the electrocardiogram (ECG) supplied by the electrocardiograph machine 64 (FIG. 7), those peaks corresponding to the closing phase of the aortic valve. The starting positions of opening and closing of the aortic valve are schematically represented by the referenced symbol 70 at different positions along the axis of time t. It is to be noted that the aortic valve 70 is closed during the parts of the ECG cycle preceding the diastole peak 66.

On periods of closing of the aortic valve, there is appreciably no backflow of blood from the ventricle. Thus, by introducing the contrast medium only during those closing phases, it will preferably enter the apertures of the left and right coronary arteries with minimum loss.

Figure 12:
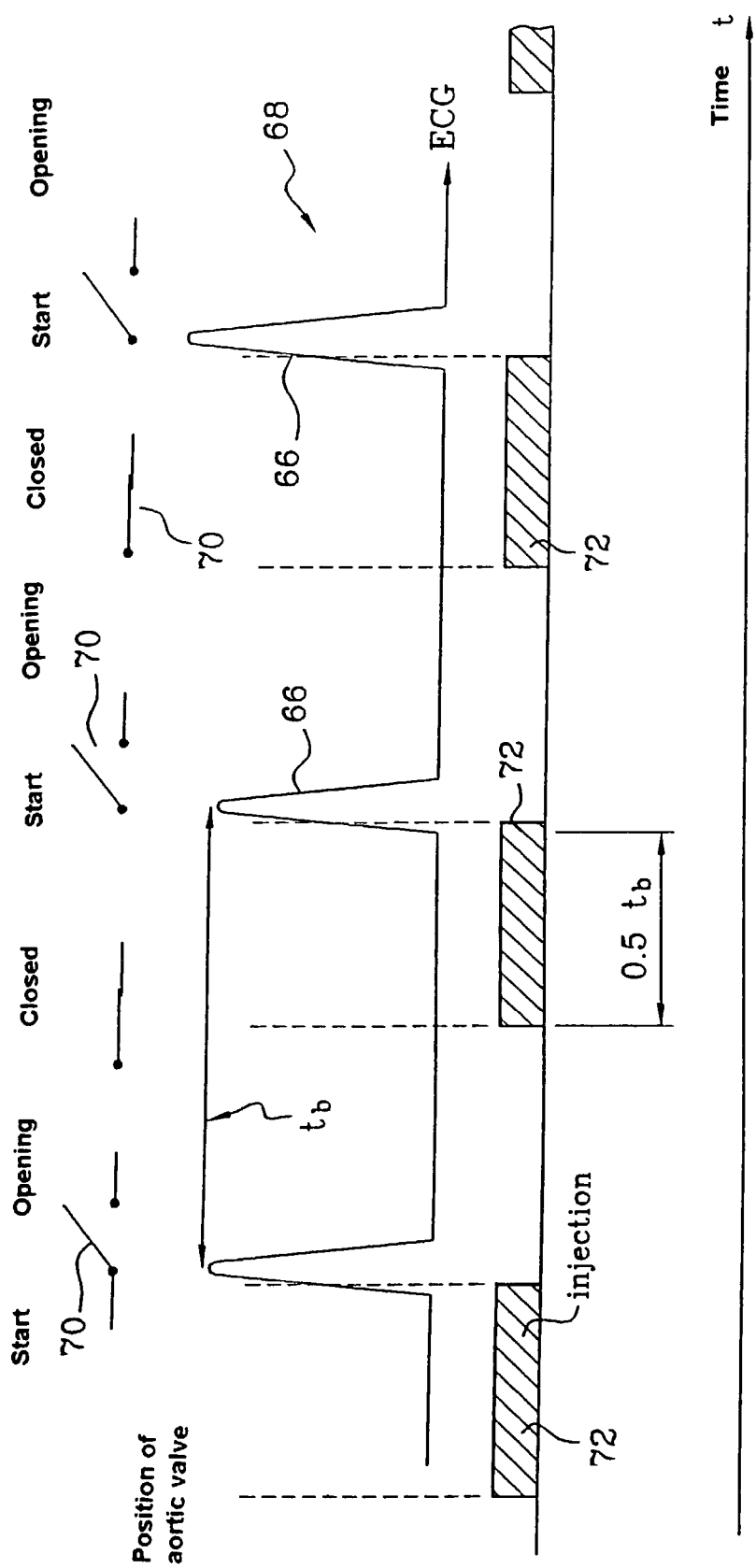
FIG. 12 is a timing diagram showing the synchronization of the cycles of introduction of contrast medium with closing of the aortic valve, with reference to the diastole peaks of a patient's electrocardiogram.

As the lower part of FIG. 12 shows, the contrast fluid injection phases (hatched rectangles 72) occupy preferably approximately half the period $t_b$ between two diastole peaks and are situated just before passing the peak. The synchronization is accomplished by the control unit 58 by automatically detecting the diastole peaks 66 and by determining their periodicity $t_b$, which makes it possible, on the one hand, to command the injector 65 to start the injection, at approximately a half-period $t_b$ after a detected peak and, on the other, to command the injector to stop the injection the moment the following peak appears.

The injector 65 is thus commanded in pulse mode to send a succession of contrast medium flows during the cycles indicated 72. The total quantity of contrast fluid injected is in the order of five to seven cubic centimeters, distributed over four or five injection cycles. The start and stop of all the injection cycles are generally synchronized respectively with the beginning and end of the image acquisition sequence of a rotation.

On that second rotation acquisition, the contrast fluid is propagated along the coronary arteries and dependent arteries in order to irrigate the myocardium. A series of images is then obtained, such as the one referenced II in FIG. 11, after subtraction and processing. In an embodiment of the invention the sequence of dynamic images thus acquired makes it possible to simultaneously visualize the entire coronary artery tree. After a few seconds of the second rotation acquisition, a part of the contrast medium will have started perfusing the myocardium.

In order to visualize that opacification of the myocardium more specifically, a third rotation acquisition is carried out after the second one and following the same path characteristics, but without injection of contrast medium (stage E32). Normally, the contrast medium injected upon the second rotation acquisition will have had enough time to diffuse properly over the entire myocardium during the period of the third rotation acquisition, without it being necessary to mark a pause time after the second rotation acquisition. Such pause time can, however, be envisaged, if necessary. The third rotation acquisition thus makes it possible to obtain, without addition of a dose of contrast medium, a three-dimensional visualization of the wall of the left ventricle (FIG. 11, image III) and to detect the possible areas of the myocardium poorly irrigated because of obstructions of the blood vessels.

Figure 11:
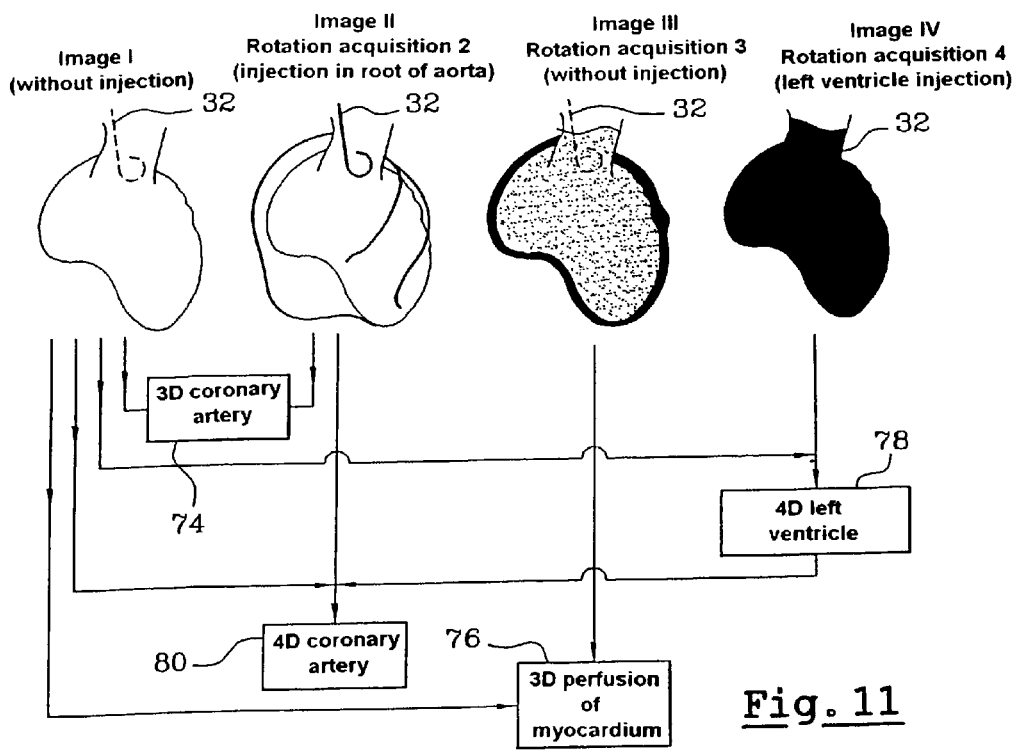
FIG. 11 is a diagram showing the opacifications on each of the four rotation acquisitions made, in the form of respective standard images designated I to IV, the figure also indicating the types of 3D and 4D images possible from different acquisitions.

The embodiment of the invention makes it possible to continue with a ventriculographic examination by pushing the pigtail catheter 32 beyond the aortic valve into the ventricle (stage E34). When the catheter 32 is thus positioned, a fourth rotation acquisition is carried out with injection of contrast fluid (E36). The path for that acquisition can be the same as for the three preceding ones or can be different, depending on the images desired for that examination. During this period, approximately 40 cubic centimeters of contrast fluid are introduced at constant flow. The dynamic acquisitions upon that fourth rotation acquisition make it possible to visualize the course of the contrast fluid in the left ventricle (FIG. 11, image IV). An evolving three-dimensional image is thus obtained, associated with the time variable which gives a four-dimensional (4D) image.

At the end of the protocol, the pigtail catheter 32 is withdrawn (stage E38). From the set of images obtained upon the rotation acquisitions, different digital processings are possible in order to obtain static (3D) or evolving (4D) three-dimensional views.

As shown in the lower part of FIG. 11, it is possible to extract from those acquisitions the following views: (1) the group of coronary arteries in 3D, by subtraction of the corresponding images of the first and second rotation acquisitions (images II–images I) and digital calculation from reference films (box 74); (2) the muscular tissue (myocardium) of the heart in 3D by subtraction of the corresponding images of the first and third rotation acquisitions (images III–images I) and digital calculation from reference films (box 76); (3) the interior of the left ventricle in 4D by subtraction of the corresponding images of the first and fourth rotation acquisitions (images IV–images I) (box 78); in that case, the first rotation acquisition will also include dynamic images synchronized with those of the fourth rotation acquisition, and (4) the group of coronary arteries in 4D by digital combination of the views of those arteries in 3D with the views in 4D of the left ventricle (box 80).

The disclosed embodiment of the invention thus provide that: (1) all of the views indicated are obtained with the use of a single catheter 32 and a single injection of contrast medium; (2) the contrast medium is introduced simultaneously in the left coronary artery and in the right coronary artery, which makes it possible to visualize in a single sequence the opacification of all of the coronary arteries; (3) it is possible to obtain, some instants after injection of the contrast fluid in the coronary arteries and by simple repetition of a rotation acquisition, a view of the opacification of the tissues of the myocardium, which enables irrigation defects to be clearly detected; (4) by simple prolongation of the advance of the catheter into the left ventricle, the protocol can be continued with a dynamic examination of the movements of that part of the heart; and (5) introducing the contrast fluid into the left and right coronary arties solely during the phases of closing of the aortic valve, according to an embodiment, alone makes it possible to reduce the dose by approximately 50% or to make acquisitions over period twice as long at equal dose.

Thus, a single stage of introduction of the contrast medium suffices to enable the structure of the coronary arterial tree to be visualized from the left and right coronary arteries. The fact that the image plane is made to file by upon acquisition makes possible a three-dimensional reconstruction of that structure by digital processing. It is to be noted that this possibility is hard to conceive of in the standard approach described in the introduction, where the planes are instead static.

The contrast medium is advantageously introduced cyclically during the dynamic image acquisition, each cycle of introduction corresponding to a phase of closing of the aortic valve in the cardiac rhythm. Thus, the dose of contrast medium is delivered in spurts and only at times during which the product is in a relatively static environment and therefore has the best chance of entering the two coronary arteries. This arrangement can be obtained subject to a diastole peak detected on the electrocardiogram of the heart examined. In a embodiment, each cycle of introduction of the contrast medium is begun at an instant situated roughly midway between a first and a second successive diastole peak and is interrupted approximately upon the appearance of that second peak. The path of the image plane advantageously defines a left curve evolving around the patient's head-to-toe axis and left-right axis. The path can define a loop, open or closed, with one part corresponding to a movement in a first direction around the head-to-toe axis and a second part corresponding to a movement in a second direction around the head-to-toe axis opposite to the first one. The path preferably embraces points of passage corresponding to reference angulations, the rate of procession of the image plane being increased outside the points of passage and reduced at the points of passage.

The procession of the image plane is advantageously synchronized with the cardiac rhythm, so that the moment of passage on each reference angulation is situated at a same phase of the cardiac cycle, notably in the systole phase of the heart.

An image subtraction technique may be used, in which, the method can further entail a preliminary stage consisting of acquiring a dynamic image sequence with procession of the image plane on the given path, without introduction of contrast medium.

The method can also provide a stage, following stage b), comprising acquiring a new dynamic image sequence with procession of the image plane, without introduction of contrast medium, making it possible to visualize the opacification of the myocardium. The examination can be continued by ventriculography, with injection of contrast medium and parallel acquisition of dynamic images with procession of the image plane.

Stage a) of introduction of the contrast medium is preferably carried out with the aid of a so-called "Pigtail" catheter or the like.

The acquired images are advantageously processed in order to make at least one of the following: (1) a three-dimensional reconstruction of the heart not opacified; (2) a three-dimensional reconstruction of the myocardium; (3) a three-dimensional reconstruction of the coronary artery tree evolving in time, and (4) a three-dimensional reconstruction of the left ventricle evolving in time.

It can thus be guided to inject the contrast medium only during closing of the aortic valve. For that purpose, it can contain an electrocardiogram signal input and means of detection of diastole peaks in that signal, the injection being interrupted on detection of a diastole peak.

The device can contain means of starting the injection of contrast medium at a predetermined time, which can be programmable, before the arrival of a diastole peak. This time can be roughly midway between two successive diastole peaks. The device can be further programmable to inject the contrast medium over a given number of injection cycles. The device can further contain means of synchronization of the overall start and stop of injection with the start and stop of a filming sequence.

Various modifications in structure and/or steps and/or function may be made by one skilled in the art without departing form the scope and extent of the invention as recited in the claims.

What is claimed is:

1. A method of radiological examination comprising:
   introducing a contrast medium with the aid of a pigtail catheter simultaneously in a left coronary artery and in a right coronary artery from the root of an aorta and, in parallel;
   acquiring a sequence of dynamic images of propagation of the contrast medium in the left and right coronary arteries with procession of an image plane, upon acquisition of the images, on a given path; and
   acquiring a new dynamic image sequence with the procession of the image plane, without introduction of contrast medium.

2. The method according to claim 1 wherein the contrast medium is introduced cyclically during the dynamic image acquisition, each cycle of introduction corresponding to a phase of closing of an aortic valve in the cardiac rhythm.

3. The method according to claim 2 wherein each cycle of introduction of contrast medium is controlled subject to a diastole peak detected on an electrocardiogram of the heart examined.

4. The method according to claim 3 wherein each cycle of introduction of the contrast medium is begun at an instant situated roughly midway between a first and a second successive diastole peak and is interrupted approximately upon the appearance of the second peak.

5. The method according to claim 4 wherein the path of the center of the image plane defines a left curve evolving around a longitudinal axis and a left-right axis.

6. The method according to claim 4 wherein the path defines a loop, open or closed, with one part corresponding to a movement in a first direction around a longitudinal axis and a second part corresponding to a movement in a second direction around the longitudinal axis opposite the first one.

7. The method according to claim 4 wherein the path embraces points of passage corresponding to reference angulations, the rate of procession of the image plane being increased outside the points of passage and reduced at the points of passage.

8. The method according to claim 4 wherein the examination is continued by ventriculography, with injection of contrast medium and parallel acquisition of dynamic images with procession of the image plane.

9. The method according to claim 3 wherein the path of the center of the image plane defines a left curve evolving around a longitudinal axis and a left-right axis.

10. The method according to claim 3 wherein the pat defines a loop, open or closed, with one part corresponding to a movement in a first direction around a longitudinal axis and a second part corresponding to a movement in a second direction around the longitudinal axis opposite the first one.

11. The method according to claim 3 wherein the path embraces points of passage corresponding to reference angulations, the rate of procession of the image plane being increased outside the points of passage and reduced at the points of passage.

12. The method according to claim 3 wherein the examination is continued by ventriculography, with injection of contrast medium and parallel acquisition of dynamic images with procession of the image plane.

13. The method according to claim 3 wherein the acquired images are processed to make a three-dimensional reconstruction of the heart not opacified.

14. The method according to claim 2 wherein the path of the center of the image plane defines a left curve evolving around a longitudinal axis and a left-right axis.

15. The method according to claim 2 wherein the path defines a loop, open or closed, with one part corresponding to a movement in a first direction around a longitudinal axis and a second part corresponding to a movement in a second direction around the longitudinal axis opposite the first one.

16. The method according to claim 2 wherein the path embraces points of passage corresponding to reference angulations, the rate of procession of the image plane being increased outside the points of passage and reduced at the points of passage.

17. The method according to claim 2 wherein the examination is continued by ventriculography, with injection of contrast medium and parallel acquisition of dynamic images with procession of the image plane.

18. The method according to claim 2 wherein the acquired images are processed to make a three-dimensional reconstruction of the heart not opacified.

19. The method according to claim 1 wherein the path of the center of the image plane defines a left curve evolving around a longitudinal axis and a left-right axis.

20. The method according to claim 19 wherein the path defines a loop, open or closed, with one part corresponding to a movement in a first direction round a longitudinal axis and a second part corresponding to a movement in a second direction around the longitudinal axis opposite the first one.

21. The method according to claim 19 wherein the path embraces points of passage corresponding to reference angulations, the rate of procession of the image plane being increased outside the points of passage and reduced at the points of passage.

22. The method according to claim 19 wherein the examination is continued by ventriculography, with injection of contrast medium and parallel acquisition of dynamic images with procession of the image plane.

23. The method according to claim 1 wherein the path defines a loop, open or closed, with one part corresponding to a movement in a first direction around a longitudinal axis and a second part corresponding to a movement in a second direction around the longitudinal axis opposite the first one.

24. The method according to claim 23 wherein the path embraces points of passage corresponding to reference angulations, the rate of procession of the image plane being increased outside the points of passage and reduced at the points of passage.

25. The method according to claim 23 wherein the examination is continued by ventriculography, with injection of contrast medium and parallel acquisition of dynamic images with procession of the image plane.

26. The method according to claim 1 wherein the path embraces points of passage corresponding to reference angulations, the rate of procession of the image plane being increased outside the points of passage and reduced at the points of passage.

27. The method according to claim 26 wherein the procession of the image plane is synchronized with the cardiac rhythm, so that the moment of passage on each reference angulation is situated at a same phase of the cardiac cycle.

28. The method according to claim 27 wherein the moments of passage on each reference angulation correspond to the systole phase of the heart.

29. The method according to claim 28, wherein the examination is continued by ventriculography, with injection of contrast medium and parallel acquisition of dynamic images with procession of the image plane.

30. The method according to claim 27, wherein the examination is continued by ventriculography, with injection of contrast medium and parallel acquisition of dynamic images with procession of the image plane.

31. The method according to claim 26 wherein the examination is continued by ventriculography, with injection of contrast medium and parallel acquisition of dynamic images with procession of the image plane.

32. The method according to claim 1 wherein the examination is continued by ventriculography, with injection of contrast medium and parallel acquisition of dynamic images with procession of the image plane.

33. The method according to claim 1 wherein the acquired images are processed to make a three-dimensional reconstruction of the heart not opacified.

34. The method according to claim 1 wherein acquired images are processed in order to make a three-dimensional reconstruction of the myocardium.

35. The method according to claim 1 wherein acquired images are processed in order to make a three-dimensional reconstruction of the coronary tree evolving in time.

36. The method according to claim 1 wherein the acquired images are processed in order to make a three-dimensional reconstruction of the left ventricle evolving in time.

37. An apparatus comprising:
means for providing a source of radiation to an anatomical structure;
means for detecting the radiation alter pausing through the anatomical structure;
means for providing an image of the anatomical structure after the radiation has passed through the anatomical structure;
means for injection of a contrast medium with a pigtail catheter for cardiac radiology simultaneously in a left coronary and a right coronary from the root of an aorta;
means for guiding the catheter by a signal detecting cardiac rhythms, so as to inject the contrast medium during cycles synchronized with given phases of the cardiac rhythm;
means for acquiring a sequence of dynamic images of propagation of the contrast medium in the left and right coronary arteries with procession of an image plane, upon acquisition of the images, in a given path; and
means for acquiring a new dynamic image sequence with the procession of the image plan, without introduction of contrast medium.

38. An article of manufacture comprising:
a computer readable medium having computer readable program code means embodied therein, the computer readable program code means for causing a computer to carry out the method of claim 1.

39. A computer program product comprising:
a computer usable medium having computer readable program code means embedded in the medium, the computer readable program code means for carrying out the method of claim of claim 1.

40. A program storage device readable, by a machine, tangibly embodying a program of instructions executable by the machine to perform method steps, the method stops comprising to steps of claim 1.

41. A method of radiological examination comprising:
before introducing a contrast medium in a left coronary artery and in a right coronary artery from the root of an aorta acquiring a dynamic image sequence with procession of an image plane upon acquisition of the image sequence, on a given path;
introducing a contrast medium with the aid of a pigtail catheter simultaneously in the left coronary artery and in to right coronary artery from the root of the aorta and, in parallel;
acquiring a further sequence of dynamic images of propagation of the contrast medium in the left and right coronary arteries with procession of the image plane, upon acquisition of the further images, on the given path.

42. An article of manufacture comprising:
a computer readable medium having computer readable program code means embodied therein, the computer readable program code means for causing a computer to carry out the method of claim 41.

43. A computer program product comprising:
a computer usable medium have computer readable program code means embedded in the medium, the computer readable program code means for carrying out the method of claim of claim 41.

44. A program storage device readable by a machine, tangibly embodying a program of instructions executable by the machine to perform method steps, the method steps comprising the steps of claim 41.

45. An apparatus for radiological examination comprising:
   means for providing a source of radiation to an anatomical structure;
   means for detecting the radiation alter passing through the anatomical structure;
   means for providing an image of the anatomical structure after the radiation has passed through the anatomical structure;
   means for injection of a contrast medium with a pigtail catheter for cardiac radiology simultaneously in a left coronary and a right coronary from the root of an aorta;
   means for guiding the catheter by a signal detecting cardiac rhythms, so as inject the contrast medium during cycles synchronized with given phases of the cardiac rhythm;
   means for acquiring a dynamic image sequence with procession of an image plane upon acquisition of the image sequence, on a given path before introducing the contrast medium in the left coronary artery and in the right coronary artery from the root of the aorta;
   means for acquiring a sequence of dynamic images of propagation of the contrast medium in the left and right coronary arteries with procession of an image plane, upon acquisition of the images, in a given path; and
   means for acquiring a new dynamic image sequence with the procession of the image plane, after introducing the contrast medium and without addition of the contrast medium.

* * * * *

UNITED STATES PATENT AND TRADEMARK OFFICE
CERTIFICATE OF CORRECTION

PATENT NO. : 7,065,395 B2
APPLICATION NO. : 10/295055
DATED : June 20, 2006
INVENTOR(S) : Jean Lienard et al.

It is certified that error appears in the above-identified patent and that said Letters Patent is hereby corrected as shown below:

Column 1:
Line 32, after "and", delete "venticulography" and insert therefor --ventriculography--.
Line 35, after "taken", delete "form" and insert therefor --from--.
Line 66, before "and", delete "loft" and insert therefor --left--.

Column 2:
Line 3, after "which", delete "it".

Column 3:
Line 19, before "32c" insert --tip--.

Column 9:
Line 19, after "indicated", insert --at--.

Column 10:
Line 61, before "embodiment", delete "a" and insert there for --an--.

Column 11:
Line 53, after "departing", delete "form" and insert therefor --from--.

Column 12:
Line 34, after "wherein the", delete "pat" and insert therefor --path--.

Column 13:
Line 9, after "direction", delete "round" and insert therefor --around--.

Column 14:
Line 13, after "radiation", delete "alter pausing" and insert therefor --after passing--.
Line 30, after "image", delete "plan" and insert therefor --plane--.
Line 41, before "1", delete "of claim".
Line 44, after "the method", delete "stops" and insert therefor --steps--.
Line 45, after "comprising", delete "to" and insert therefor --the--.
Line 54, after "in", delete "to" and insert therefor --the--.

Column 15:
Line 2, after "medium", delete "have" and insert therefor --having--.
Line 5, before "41", delete "of claim".
Line 14, after "radiation", delete "alter" and insert therefor --after--.

UNITED STATES PATENT AND TRADEMARK OFFICE
CERTIFICATE OF CORRECTION

PATENT NO. : 7,065,395 B2
APPLICATION NO. : 10/295055
DATED : June 20, 2006
INVENTOR(S) : Jean Lienard et al.

It is certified that error appears in the above-identified patent and that said Letters Patent is hereby corrected as shown below:

<u>Column 16</u>:
Line 2, after "as", insert --to--.

Signed and Sealed this

Sixth Day of February, 2007

JON W. DUDAS
*Director of the United States Patent and Trademark Office*